US010994137B2

(12) United States Patent
Koning et al.

(10) Patent No.: US 10,994,137 B2
(45) Date of Patent: May 4, 2021

(54) NEURAL STIMULATION SYSTEM

(71) Applicant: ADVANCED BIONICS AG, Staefa (CH)

(72) Inventors: Raphael Sebastian Koning, Wedemark (DE); Volkmar Hamacher, Hannover (DE)

(73) Assignee: Advanced Bionics AG, Staefa (CH)

( * ) Notice: Subject to any disclaimer, the term of this patent is extended or adjusted under 35 U.S.C. 154(b) by 130 days.

(21) Appl. No.: 16/097,676

(22) PCT Filed: May 9, 2016

(86) PCT No.: PCT/EP2016/060315
§ 371 (c)(1),
(2) Date: Oct. 30, 2018

(87) PCT Pub. No.: WO2017/194084
PCT Pub. Date: Nov. 16, 2017

(65) Prior Publication Data
US 2019/0134397 A1 May 9, 2019

(51) Int. Cl.
*A61N 1/36* (2006.01)
*H04R 25/00* (2006.01)
(52) U.S. Cl.
CPC ..... *A61N 1/36038* (2017.08); *A61N 1/36036* (2017.08); *A61N 1/36062* (2017.08);
(Continued)
(58) Field of Classification Search
CPC .. A61N 1/36; A61N 1/36036; A61N 1/36038; A61N 1/36062; H04R 25/558;
(Continued)

(56) References Cited

U.S. PATENT DOCUMENTS 5,522,865 A * 6/1996 Schulman .......... A61N 1/36185
607/32
5,531,774 A * 7/1996 Schulman .......... A61N 1/36185
607/55
(Continued)

FOREIGN PATENT DOCUMENTS

WO 2015/041639 3/2015
WO 2015/147773 10/2015

OTHER PUBLICATIONS

International Search Report and Written Opinion received in International Application No. PCT/EP16/060315, dated Jul. 20, 2016.

*Primary Examiner* — Christopher A Flory
(74) *Attorney, Agent, or Firm* — ALG Intellectual Property, LLC

(57) ABSTRACT

A neural stimulation system comprises a microphone arrangement for capturing an audio signal from ambient sound, a sound processor unit, a headpiece, and an implantable neural stimulator, the sound processor unit comprising a housing to be worn behind a patient's ear or at a patient's body, and a signal processing unit within the sound processor unit housing for generating a neural stimulation signal from the captured audio signal, the sound processor being communicatively coupled to the headpiece for supplying the neural stimulation signal to the headpiece, the headpiece comprising a housing separate from the housing of the sound processor and to be fixed at the patient's head, a signal transmission unit for transmitting the neural stimulation signal to a signal receiving unit of the implantable cochlear stimulator, and a user interface for controlling operation of the sound processor unit.

21 Claims, 4 Drawing Sheets

(52) U.S. Cl.
CPC .......... *H04R 25/558* (2013.01); *H04R 25/65* (2013.01); *H04R 2225/55* (2013.01); *H04R 2225/67* (2013.01)

(58) Field of Classification Search
CPC . H04R 25/65; H04R 2225/55; H04R 2225/67
See application file for complete search history.

(56) References Cited

U.S. PATENT DOCUMENTS

| | | | | |
|---|---|---|---|---|
| 5,569,307 | A * | 10/1996 | Schulman | A61N 1/36185 607/55 |
| 5,603,726 | A * | 2/1997 | Schulman | A61N 1/36185 607/57 |
| 5,609,616 | A * | 3/1997 | Schulman | A61N 1/36185 607/56 |
| 5,776,172 | A * | 7/1998 | Schulman | A61N 1/36185 607/55 |
| 5,824,022 | A | 10/1998 | Zilberman et al. | |
| 5,876,425 | A * | 3/1999 | Gord | A61N 1/36185 607/33 |
| 5,938,691 | A * | 8/1999 | Schulman | A61N 1/36038 607/57 |
| 6,073,050 | A * | 6/2000 | Griffith | A61N 1/37223 340/870.24 |
| 6,321,118 | B1 * | 11/2001 | Hahn | A61N 1/36036 607/61 |
| 7,561,708 | B2 | 7/2009 | Rohrlein | |
| 8,824,712 | B2 | 9/2014 | Sacha | |
| 8,885,856 | B2 | 11/2014 | Sacha | |
| 2005/0209657 | A1 * | 9/2005 | Chung | A61N 1/36036 607/57 |
| 2006/0190059 | A1 * | 8/2006 | Griffith | A61N 1/36036 607/57 |
| 2007/0014423 | A1 * | 1/2007 | Darbut | H04R 25/65 381/330 |
| 2007/0127757 | A2 * | 6/2007 | Darbut | H04R 25/65 381/330 |
| 2007/0179565 | A1 * | 8/2007 | Overstreet | A61N 1/36038 607/57 |
| 2007/0282394 | A1 * | 12/2007 | Segel | A61N 1/36038 607/57 |
| 2008/0221640 | A1 * | 9/2008 | Overstreet | A61N 1/36036 607/48 |
| 2010/0046778 | A1 | 2/2010 | Crawford et al. | |
| 2010/0272299 | A1 * | 10/2010 | Van Schuylenbergh | H04R 25/554 381/315 |
| 2010/0280307 | A1 * | 11/2010 | Lineaweaver | A61N 1/36036 600/25 |
| 2011/0046730 | A1 * | 2/2011 | Meskens | A61N 1/36036 623/10 |
| 2012/0029593 | A1 * | 2/2012 | Calle | A61N 1/37264 607/57 |
| 2012/0029594 | A1 * | 2/2012 | Chapa | A61N 1/36038 607/57 |
| 2012/0029595 | A1 * | 2/2012 | Kruger | A61N 1/36038 607/57 |
| 2012/0029930 | A1 * | 2/2012 | Calle | G06F 16/252 705/2 |
| 2012/0041515 | A1 * | 2/2012 | Meskens | A61N 1/36038 607/57 |
| 2012/0053656 | A1 * | 3/2012 | Chapa | H04R 25/70 607/57 |
| 2012/0150259 | A1 * | 6/2012 | Meskens | A61N 1/3787 607/57 |
| 2013/0195298 | A1 | 8/2013 | Sacha | |
| 2013/0204326 | A1 * | 8/2013 | Vanpoucke | A61N 1/36036 607/57 |
| 2014/0012351 | A1 * | 1/2014 | Calle | A61N 1/37235 607/57 |
| 2014/0025138 | A1 | 1/2014 | Meskens et al. | |
| 2014/0086439 | A1 * | 3/2014 | Johnston | A61N 1/36039 381/314 |
| 2014/0114375 | A1 * | 4/2014 | Chapa | H04R 25/50 607/57 |
| 2014/0135872 | A1 * | 5/2014 | Saoji | A61N 1/36039 607/57 |
| 2015/0012058 | A1 * | 1/2015 | Crawford | H04R 25/652 607/57 |
| 2015/0049892 | A1 * | 2/2015 | Petersen | H04R 25/554 381/315 |
| 2015/0051654 | A1 * | 2/2015 | Litvak | A61B 5/121 607/3 |
| 2015/0057714 | A1 * | 2/2015 | Litvak | H04R 25/70 607/3 |
| 2015/0119635 | A1 * | 4/2015 | Gustafsson | A61F 11/04 600/25 |
| 2015/0196759 | A1 * | 7/2015 | Meskens | H04R 25/606 600/25 |
| 2015/0360029 | A1 * | 12/2015 | Kulkarni | A61N 1/36039 607/57 |
| 2016/0089542 | A1 * | 3/2016 | Frieding | H04R 25/554 607/57 |
| 2016/0142830 | A1 * | 5/2016 | Hu | G10L 21/14 434/185 |
| 2016/0249141 | A1 * | 8/2016 | Verdooner | G10L 21/02 |
| 2016/0375243 | A1 * | 12/2016 | Roehrlein | H04R 25/602 607/57 |

* cited by examiner

NEURAL STIMULATION SYSTEM

The invention relates a neural stimulation system comprising a sound processor unit, a headpiece and an implantable neural stimulator.

Typically, a neural stimulation system, such as a cochlear implant system, comprises a sound processor (or sound processor unit, which terms hereinafter are used interchangeably), which may be worn behind a patient's ear (and thus comprises a BTE ("behind-the-ear") housing) or at the patient's body, wherein the sound processor comprises a microphone arrangement for capturing an audio signal from ambient sound and a signal processing unit for generating a neural stimulation signal from the captured audio signal. The neural stimulation signal is supplied via a cable connection to a headpiece that is fixed (typically by magnetic forces) at the patient's head and comprises a signal transmission unit for transmitting the neural stimulation signal via a transcutaneous (typically wireless) link to a signal receiving unit of the implantable cochlear stimulator (the transmission unit and the receiving unit usually are coils).

Typically, the sound processor of a cochlear implant provides for a number of hearing programs for different listening scenarios. Although a classifier may be used to automatically change between, for example, a program for speech in noisy surrounding and other listening scenarios, the patient often wants to have control on the choice of the program, the loudness or other settings of the sound processor. Typically, the control of the sound processor by the patient is enabled by buttons that are on the BTE housing of the sound processor or on the housing of a body worn sound processor, or it may be enabled by accessories like remote controls of the sound processor.

Buttons on the sound processor may be difficult to use since the patient cannot see the buttons when wearing the sound processor and since the buttons are relatively small due to limited space on the sound processor housing. In particular, elderly patients often have difficulties in operating small things due to motoric impairments. On the other hand, implementing user control of the sound processor via an accessory/remote control device may be inconvenient in that such device has to be carried around in addition to the sound processor.

US 2010/0046778 A1 relates to a cochlear implant system with an integrated headpiece, wherein the headpiece includes the functionality of the sound processor, so that no sound processor separate from the headpiece is required. The headpiece may be provided with a button at the side of the housing facing away from the head of the patient for enabling the patient to switch between a number of predetermined audio programs or to adjust the amplification of the system.

U.S. Pat. No. 5,824,022 relates to a BTE sound processor including the functionality of a classical headpiece, such as the wireless transmission unit of the transcutaneous link, wherein the sound processor is provided with a user interface comprising control elements like a volume control knob, a sensitivity control knob and an on-off button.

Another example of an integrated headpiece is a device available from the company MED-EL Elektromedizinische Gerate GmbH, Innsbruck, Austria, under the product designation "Rondo", wherein the housing of the headpiece is provided with an on-off switch at the narrow side of the essentially disc-like housing.

WO 2015/147773 A1 relates to a cochlear implant system comprising a headpiece separate from a BTE-type sound processor, wherein the sound processor and the headpiece are coupled via a wireless link and wherein the headpiece is provided with an on-off switch and a knob for adjusting the transmission level of the headpiece transmitter.

WO 2015/041639 A1 relates to a BTE-type sound processor that includes various control elements, such as buttons, on the narrow side of the housing of the BTE sound processor.

U.S. Pat. No. 8,885,856 B2 relates to hearing aids of the ITE ("in-the-ear"), BTE or RIC ("receiver-in-the-canal") type including a touch sensor, such as a capacitive sensor, for being operated by the user.

U.S. Pat. No. 7,561,708 B2 relates to an ITE hearing aid comprising a proximity sensor for enabling control of the hearing aid without the need to touch a control element directly.

U.S. Pat. No. 8,824,712 B2 relates to a BTE hearing aid including a capacitive sensor as a control element to be operated by the user.

It is an object of the invention to provide for a neural stimulation system having a sound processor unit separate from the headpiece, wherein the system can be used in a convenient manner.

According to the invention, this object is achieved by a neural stimulation system as defined in claim 1.

The invention is beneficial in that, by providing the headpiece with a manually operable user interface for controlling operation of the sound processor unit, the patient can control operation of the sound processor unit, such as selecting a program or a loudness, in a particularly convenient manner, since the headpiece typically is located at a manually easily accessible position at the head and typically offers a relatively large surface area for placement of the user interface. Furthermore, this relatively large surface area can be used to provide space not only for larger controls, but also for a greater number of controls.

Preferably, the user interface is configured for being operated by the patient by manually acting on a side of the headpiece facing away from the patient's head.

Preferred embodiments of the invention are defined in the dependent claims.

Hereinafter, examples of the invention will be illustrated by reference to the attached drawings, wherein.

Figure 1:
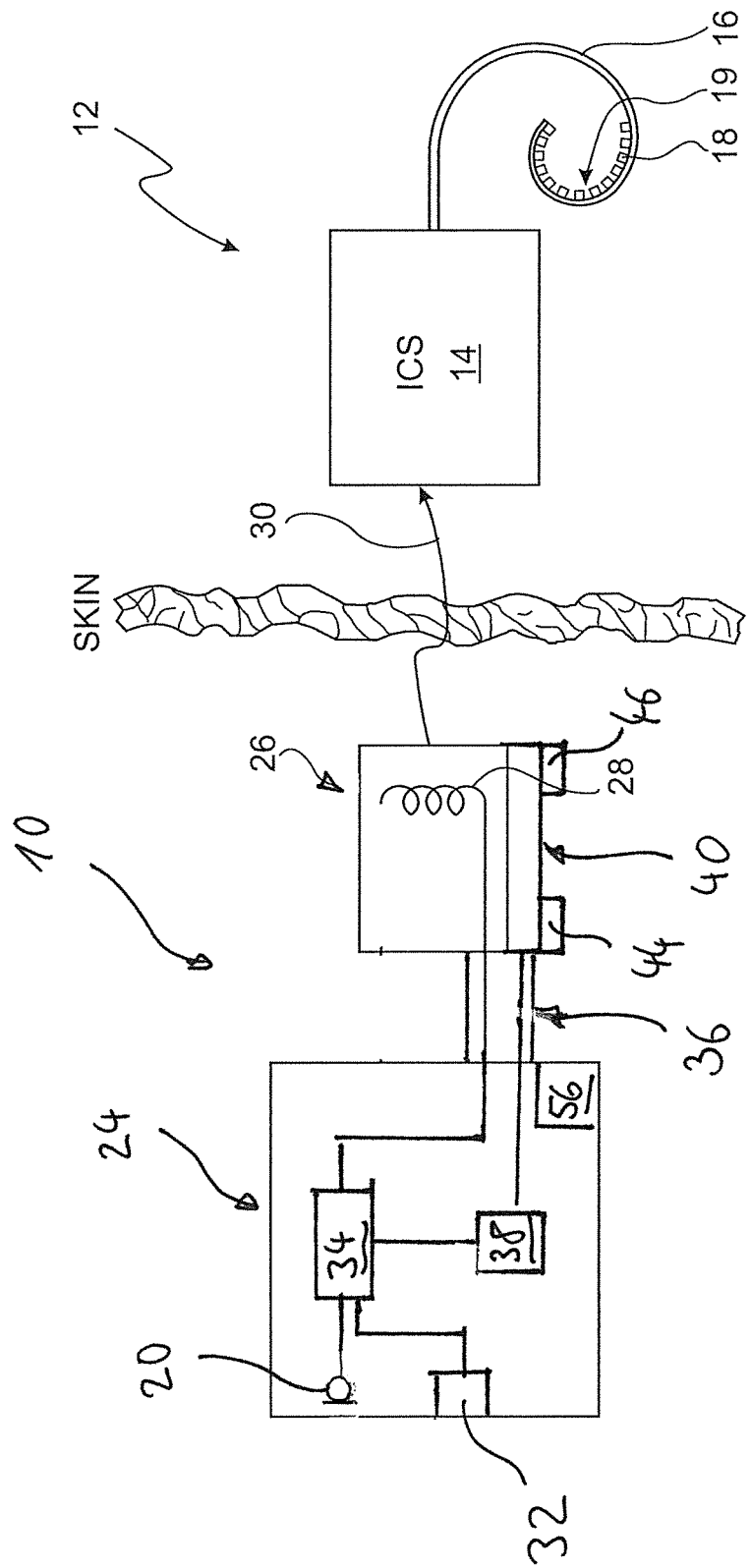
FIG. 1 is a block diagram of an example of a cochlear implant system according to the invention.

In FIG. 1 an example of a block diagram of a CI system to be used with the invention is shown schematically. The system comprises a sound processing sub-system 10 and a stimulation sub-system 12. The sound processing sub-system 10 serves to detect or sense an audio signal and divide the audio signal into a plurality of analysis channels each containing a frequency domain signal (or simply "signal") representative of a distinct frequency portion of the captured audio. A signal level value is determined for each analysis channel by analyzing the respective frequency domain signal. Stimulation parameters are generated based on the frequency domain signal and are transmitted to the stimulation sub-system 12.

Stimulation sub-system 12 serves to generate and apply electrical stimulation (also referred to herein as "stimulation current" and/or "stimulation pulses") to stimulation sites at the auditory nerve within the cochlea of a patient in accordance with the stimulation parameters received from the sound processing sub-system 10. Electrical stimulation is provided to the patient via a CI stimulation assembly 18 comprising a plurality of stimulation channels.

In the example shown in FIG. 1, the stimulation sub-system 12 comprises an implantable cochlear stimulator (ICS) 14, a lead 16 and the stimulation assembly 18 disposed on the lead 16. The stimulation assembly 18 comprises a plurality of stimulation contacts 19 for electrical stimulation of the auditory nerve. The stimulation assembly 18 may be inserted within a duct of the cochlea in such a manner that the stimulation contacts 19 are in communication with one or more stimulation sites within the cochlea, i.e., the stimulation contacts 19 are adjacent to, in the general vicinity of, in close proximity to, directly next to, or directly on the respective stimulation site.

In the example shown in FIG. 1, the sound processing sub-system 10 comprises a sound processor unit 24 that captures audio signals via a microphone 20 and a headpiece 26 having a coil 28 disposed therein. The sound processor unit 24 is configured to process the captured audio signals in accordance with a selected sound processing strategy to generate appropriate stimulation parameters for controlling the ICS 14 and may include, or be implemented within, a BTE unit (in the example shown in FIGS. 2 and 3 the sound processor unit 24 is implemented in BTE-type housing 50) or a portable sound processor ("PSP"). In the example of FIG. 1 the sound processor unit 24 is configured to transcutaneously transmit data (in particular, data representative of one or more stimulation parameters) to the ICS 14 via a wireless transcutaneous communication link 30. The headpiece 26 may be affixed to the patient's head and positioned such that the coil 28 is communicatively coupled to the corresponding coil (not shown) included within a signal receiving unit 54 (see FIG. 2) of the ICS 14 in order to establish the link 30. The link 30 may include a bidirectional communication link and/or one or more dedicated unidirectional communication links.

The sound processor unit 24 may comprise an audio interface 32 for receiving audio signals from an external audio source, such as a music player or a TV set. The audio interface 32 may be for a wireless or for a wired connection. The sound processor unit 24 further comprises a signal processing unit 34 for generating the neural stimulation signal from the input audio signal captured by the microphone arrangement 20 and from input audio signals supplied via the audio interface 32 (if present), with the neural stimulation signal being supplied to the headpiece 26 via a connection 36. The connection 36 preferably is a cable connection, but in principle it also could be a wireless connection. The sound processor 24 also comprises a controller 38 for controlling operation of the sound processor unit 24, in particular for controlling the signal processing unit 34 (for example by selecting the program to be presently used, the loudness to be achieved by the neural stimulation signal, etc.).

The headpiece 26 comprises a user interface 40 for being manually operated by the patient in order to control operation of the sound processor unit 24, in particular operation of the signal processing unit 34, via the controller 38; to this end, the user interface 40 is connected to the controller 38 via the connection 36. The user interface typically is provided on (or as part of) the housing of the headpiece; in some cases, the user interface may be provided even within the housing (for example, in case that the user interface comprises touchless sensor, such as a capacitive sensor or an infrared sensor).

The headpiece 26 typically is powered by a battery 56 of the sound processor unit 24 via the connection 36.

Figure 2:
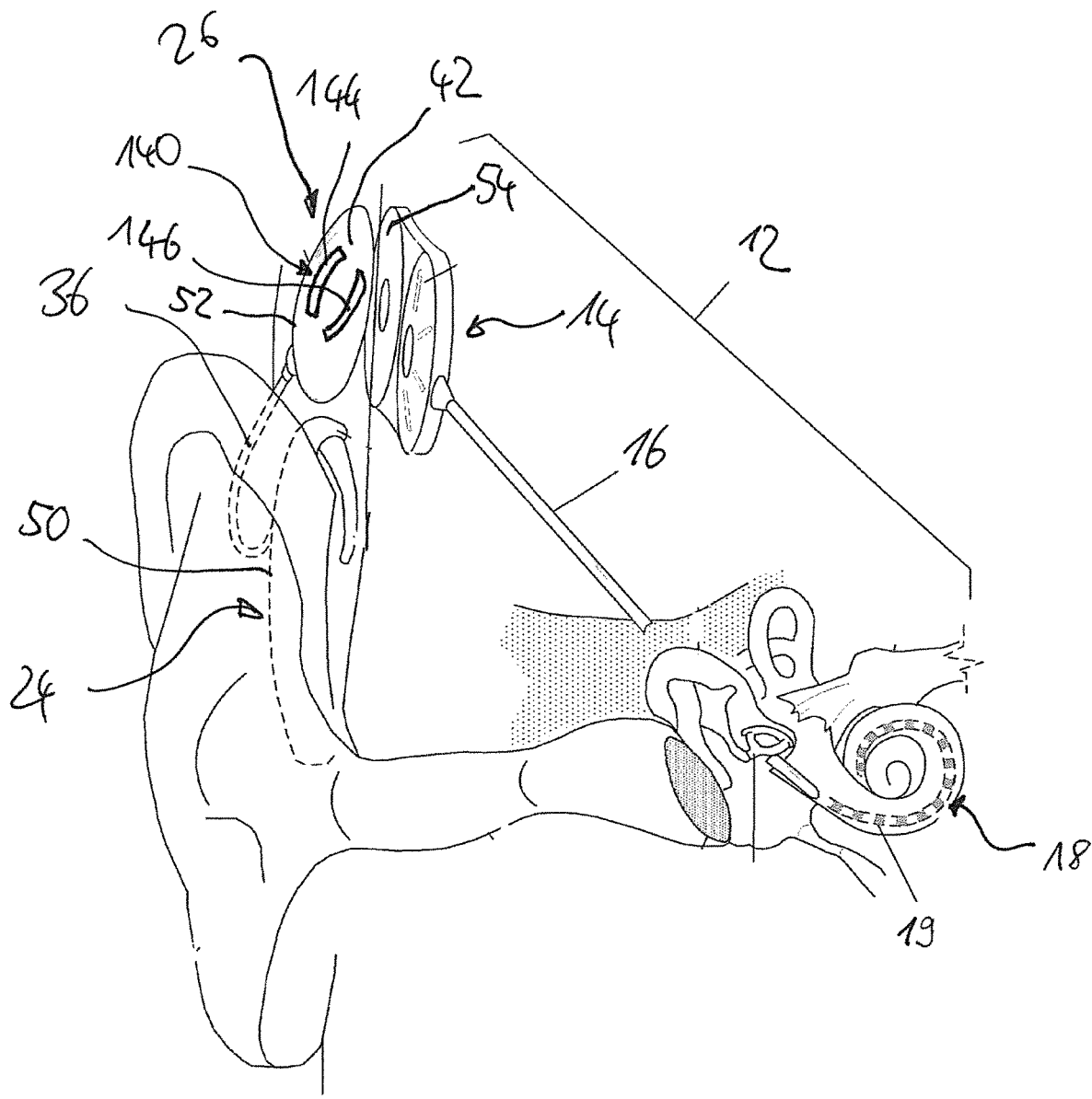
FIG. 2 is an illustrative diagram showing an example of a cochlear implant system in use.
Figure 3:
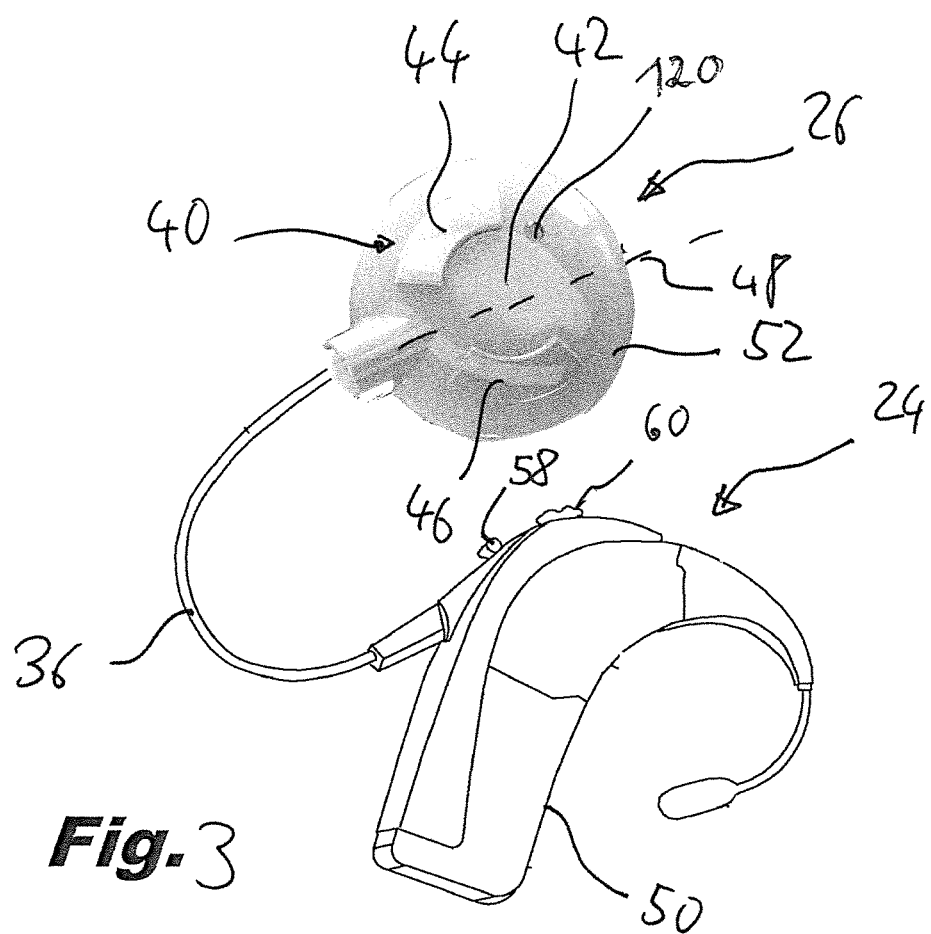
FIG. 3 is a view of an example of a sound processor and a headpiece of a cochlear implant system according to the invention.

As can be seen in FIGS. 2 and 3, the headpiece typically has a flat configuration, for example with a housing 52 having a disc-like shape, wherein the user interface 40 is configured for being operated by a patient by manually acting on a side 42 of the headpiece housing 52 facing away from the patient's head.

In general, the user interface comprises at least one control to be operated by the user.

According to one example, the user interface 40 comprises at least one button located at the side 42; in the example of FIG. 3, the user interface 40 comprises two buttons 44, 46 arranged symmetrically with regard to a symmetry axis (indicated at 48 in FIG. 3) that is oriented substantially vertical when the headpiece 26 is worn at the head, wherein the headpiece 26 is configured to be interchangeably worn at both ears, and wherein the system is configured to reverse the functionalities of mutually symmetrical buttons 44, 46 when the headpiece 26 is moved to the other ear. Such design allows the headpiece 26 to be worn at both ears, while providing the same functionality at both ears.

Each button 44, 46 may comprise a unique surface structure so that each button can be individually identified when being touched by the patient.

Figure 4:
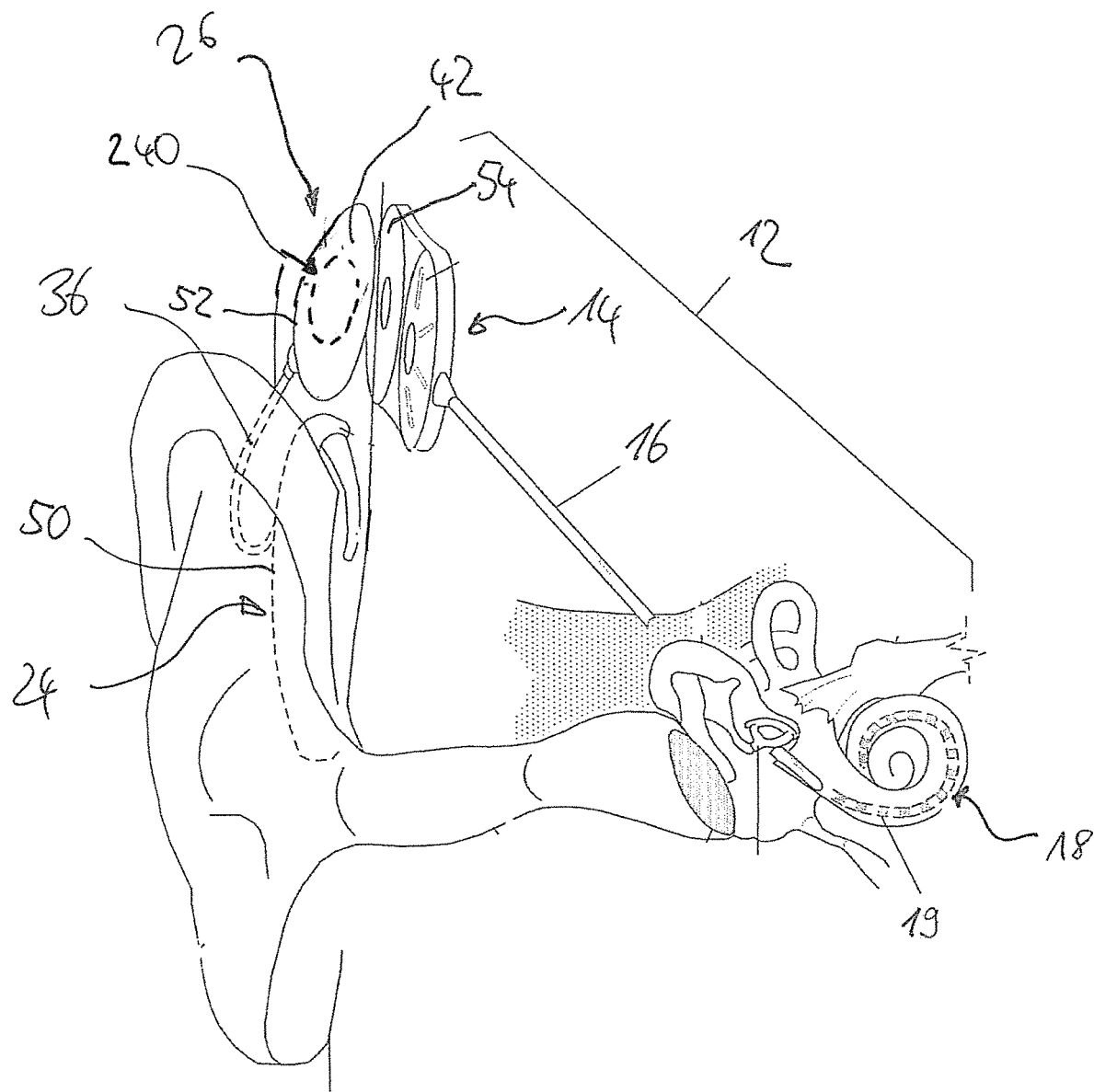
FIG. 4 is an illustrative diagram like FIG. 2, showing another example of a cochlear implant system in use.

According to another example, as shown in FIG. 4, the user interface 240 may comprise a smooth surface having no visible buttons, allowing the user to make adjustments discreetly (in FIG. 4 an externally non-visible control element is indicated by dashed lines).

According to one such example, the headpiece 26 may comprise a touch sensitive surface area of the side 42 of the housing 52 facing away from the patient's head.

According to another example, the user interface may comprise a capacitive sensor or an infrared sensor so as to enable touchless operation of the user interface, with the user interface 40 then acting as a proximity sensor. An example of such configuration of a user interface 140 is illustrated in FIG. 2, wherein the side 42 of the housing 52 facing away from the user' head comprises two surface areas 144 and 146 as controls, each surface area 144, 146 including at least one touchless sensor. Preferably, the user interface 140 may comprise a plurality of infrared sensors, so that it is possible to detect motions that are very close to the headpiece 26. The use of multiple sensors allows capturing movements of the user's hand or fingers, wherein false movements, i.e. movements having a trajectory and/or velocity outside a given range, may be detected and excluded from being accepted as a valid user action on the user interface 140.

In case that the headpiece 26 comprises a touch sensitive surface area, the surface area is preferably configured such that it can detect one or multiple contact points and movements so as to control different parameters of the settings by different gestures of the patient.

Any combination of various control mechanisms can be combined, such as buttons and a touch sensitive surface.

As indicated in FIG. 2, the user interface 40 on the headpiece 26 may be provided as an alternative to, or replacement for, controls on the sound processor unit 24, such that sound processor unit 24 has no controls, so that the user interface 140 of the headpiece 26 is provided for complete control of all controllable functions of the sound processor unit 24.

Alternatively, as shown in FIG. 3, the user interface 40 on the headpiece 26, such as buttons 44 and 46, may be provided in addition to controls 58, 60 on the sound processor unit 24. These buttons 44 and 46 may provide additional functionality, or may provide duplicate functionality, to the controls on the sound processor unit 24. In other words, in the first case, the additional user interface formed by the controls 58, 60 is provided for controlling, alternatingly with the user interface 40 of the headpiece 26, at least part of the functions of the sound processor unit which are also controllable by the user interface 40 of the headpiece 26, whereas in the second case the additional user interface formed by the control 58, 60 is provided for controlling functions of the sound processor unit 24 which are not controllable by the user interface 40 of the headpiece 26.

Preferably, the maximum dimension (e.g. the diameter or the length) of the controls 44, 46, 144, 146 is from 3 to 12 mm, the number of controls 44, 46, 144, 146 is from 1 to 8.

According to one example (see FIG. 1), the microphone arrangement 20 may form part of the sound processor unit 24; in particular, it may be integrated within the housing 50 of the sound processor unit 24.

According to an alternative example, the headpiece 26 rather than the sound processor unit 24 may be provided with a microphone arrangement (see microphone arrangement 120 in FIG. 3). In this case the audio signal captured by the microphone arrangement 120 is supplied via the connection 36 to the signal processing unit 34 of the sound processing unit 24.

According to another example, the sound processor unit 24 comprises a microphone arrangement 20 and the headpiece 26 comprises an additional microphone arrangement 120, wherein both audio signals or only one of them may be supplied to the signal processing unit 34 for being used in the generating of the neural stimulation signal. In this case the user interface 40 of the headpiece 26 may be configured to enable selection of the audio signal input to the signal processing unit 34 by the user; for example, the user may switch between the microphone arrangement 20 and 120.

According to one example, the headpiece may be configured to only control a single sound processor unit, namely that worn at the same side of the head as the headpiece. In another example, the headpiece may be configured to control two sound processor units, namely one at each side of the head, communicating wired or wirelessly with the contralateral sound processor unit.

The invention is applicable not only to electrical only stimulation systems but also to multimodal stimulation systems, such EAS (electric-acoustic stimulation) systems, wherein the controls can control aspects of multiple modes, separately or together, such as electrical stimulation applied via electrodes to the cochlear nerve and acoustic stimulation applied to a speaker.

The neural stimulator typically is configured to stimulate the patient's cochlea (typically an electrode array implanted in a cochlear duct, as in the above described examples); alternatively, the neural stimulator may be configured for intraneural stimulation or for brainstem stimulation.

The invention claimed is:

1. A neural stimulation system, comprising:
a microphone arrangement for capturing an audio signal from ambient sound, a sound processor unit, a headpiece, and an implantable neural stimulator,
the sound processor unit comprising a housing to be worn behind a patient's ear or at a patient's body, and a signal processing unit within the sound processor unit housing for generating a neural stimulation signal from the captured audio signal, the sound processor being communicatively coupled to the headpiece for supplying the neural stimulation signal to the headpiece,
the headpiece comprising a housing separate from the housing of the sound processor and to be fixed at the patient's head, a signal transmission unit for transmitting the neural stimulation signal to a signal receiving unit of the implantable neural stimulator, and a user interface for controlling operation of the sound processor unit,
wherein the user interface comprises a first button and a second button configured for being manually operated by the patient, wherein the headpiece is configured to be interchangeably worn at a first ear of the patient and a second ear of the patient, and wherein the neural stimulation system is configured to reverse functionalities of the first and second buttons when the headpiece is moved from the first ear to the second ear.

2. The system of claim 1, wherein the headpiece is powered by a battery of the sound processor unit.

3. The system of claim 1, wherein the sound processor unit and the headpiece are electrically connected via a cable connection.

4. The system of claim 1, wherein the first and second buttons are configured for being operated by the patient by manually acting on a side of the headpiece facing away from the patient's head.

5. The system of claim 1, wherein at least one of the first or second buttons comprises a touch sensitive surface area of the housing of the headpiece.

6. The system of claim 1, wherein at least one of the first or second buttons comprises a capacitive sensor.

7. The system of claim 1, wherein at least one of the first or second buttons comprises an infrared sensor.

8. The system of claim 1, wherein the first and second buttons are arranged symmetrically with regard to a symmetry axis that is oriented substantially vertical when the headpiece is worn at the head.

9. The system of claim 1, wherein the first and second buttons each comprise a unique surface structure so that each of the first and second buttons button can be identified when touched by the patient.

10. The system of claim 1, wherein the microphone arrangement forms part of the sound processor unit.

11. The system of claim 10, wherein the microphone arrangement integrated within the housing of the sound processor unit.

12. The system of claim 1, wherein the headpiece comprises an additional microphone for capturing an additional audio signal from ambient sound, which additional audio signal is to be supplied to the signal processing unit for being used in the generating of the neural stimulation signal.

13. The system of claim 12, wherein the user interface of the headpiece is configured to enable selection of the audio signal input to the signal processing unit from the audio signal captured by the microphone arrangement and the additional audio signal captured by the additional microphone arrangement.

14. The system of claim 1, wherein the microphone arrangement forms part of the headpiece.

15. The system of claim 1, wherein the sound processor unit is configured such that the user interface of the headpiece is provided for complete control of all controllable functions of the sound processor unit.

16. The system of claim 1, wherein the sound processor unit comprises an additional user interface for controlling functions of the sound processor unit which are not controllable by the user interface of the headpiece, the additional user interface being configured for being manually operated by the patient.

17. The system of claim 1, wherein the sound processor unit comprises an additional user interface for controlling, alternatingly with the user interface of the headpiece, at least part of the functions of the sound processor unit which are also controllable by the user interface of the headpiece.

18. The system of claim 1, wherein the implantable neural stimulator is a cochlea stimulator.

19. A headpiece for use in a neural stimulation system, the headpiece comprising:
 a housing configured to be fixed at a head of a user;
 a signal transmission unit for transmitting a neural stimulation signal from a sound processor unit to a signal receiving unit of an implantable neural stimulator; and
 a user interface for controlling operation of the sound processor unit;
 wherein the user interface comprises a first button and a second button configured for being manually operated by the user, wherein the headpiece is configured to be interchangeably worn at a first ear of the patient and a second ear of the patient, and wherein the headpiece is configured to reverse functionalities of the first and second buttons when the headpiece is moved from the first ear to the second ear.

20. The headpiece of claim 19, wherein the headpiece is powered by a battery of the sound processor unit.

21. The headpiece of claim 19, wherein the sound processor unit and the headpiece are electrically connected via a cable connection.

* * * * *